United States Patent
Sawatzki et al.

(10) Patent No.: US 6,355,297 B1
(45) Date of Patent: Mar. 12, 2002

(54) PROTEIN COMPONENT FOR DIETETIC FOOD

(75) Inventors: Günther Sawatzki, Munzenberg; Gilda Georgi, Friedrichsdorf; Günther Böhm, Echzell, all of (DE)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 09/774,189

(22) PCT Filed: Aug. 11, 1999

(86) PCT No.: PCT/EP99/05877

§ 371 Date: Feb. 6, 2001

§ 102(e) Date: Feb. 6, 2001

(87) PCT Pub. No.: WO00/08946

PCT Pub. Date: Feb. 24, 2000

(30) Foreign Application Priority Data

Aug. 11, 1998 (DE) .......................... 198 36 338

(51) Int. Cl.[7] .............................. A23J 3/10; A23L 1/305; A23C 1/187; A23C 3/00; A21D 4/00
(52) U.S. Cl. ........................ 426/657; 426/801; 426/580; 426/334; 426/330.2
(58) Field of Search ............................... 426/657, 801, 426/580, 330.2, 334; 530/832, 360

(56) References Cited

U.S. PATENT DOCUMENTS 5,068,118 A    11/1991    Strandholm
6,190,724 B1 *   2/2001    Sawatzki et al.

FOREIGN PATENT DOCUMENTS

WO    0 745 330 A    12/1996
WO    WO 97 05785 A   2/1997

OTHER PUBLICATIONS

Chemical Abstracts, vol. III, Sep. 11, 1989, Abstract No. 95808, E. Li–Chan, S. Nakan: "Enzymic dephosphorylation of bovine casein to improve acid clotting properties and digestibility for infant formula", XP002017623, Zusammenfassung & Journal of Dairy Research, 1989.

Database FSTA 'Online! International Food Information Service (IFIS), Frankfurt/Main, De Hekken D L Van et al.: "Functional properties of dephosphorylated bovine whole casein." Database accession No. 94–1–02–p0022 XP002126135, Zusammenfassung & Journal of Dairy Science, 1993.

Database FSTA 'Online! International Food Information Service (IFIS), Frankfurt/Main, De Meisel H et al.: Database accession No. 96–1–06–p0082 XP002126136, Zusammenfassung & Kieler Milchwirtschaftliche Forschungsberichte, 1995.

* cited by examiner

Primary Examiner—Anthony J. Weier
(74) Attorney, Agent, or Firm—Bacon & Thomas

(57) ABSTRACT

The invention relates to the use of a protein component based on conventional proteins used for the production of foods, at least 20 wt-% thereof having a phosphate residue, which is covalently bound to the protein, whereby 50 to 100 wt-% of the proteins including at least one covalently bound phosphate residue, are subjected to a dephosphorylation reaction wherein 20 to 100% of the covalently bound phosphate residues were removed, for a treatment of adult and adolescent patients, as well as of babies and small children suffering from a disturbed gastrointestinal motility and of reflux-predisposed patients. The use of said protein component not only allows for a sufficient protein supply but it also passes rapidly through the stomach and prevents the stomach contents from flowing back into the oesophagus.

15 Claims, No Drawings

PROTEIN COMPONENT FOR DIETETIC FOOD

The invention relates to the use of a protein component for dietetic food products based on conventional proteins used for the production of foods for the treatment of patients suffering from a disturbed gastrointestinal motility and of reflux-predisposed patients, and of a food product containing said proteins.

A delayed stomach emptying after a meal is a main symptom of patients suffering from a disturbed gastrointestinal motility. One of the most important consequences of a delayed stomach emptying is the return transportation of stomach contents into the oesophagus, the so-called gastro-oesophageal reflux ("reflux" in the following). The consequences are, for one, damages of the oesophageal mucous membrane caused by gastric acid and the enzymes of the gastric juice, which, with frequent occurrence, leads to an inflammatory alteration of the oesophagus, the so-called gastro-oesophageal reflux disease. Another consequence may be emesis. The latter would cause the danger of an aspiration of stomach contents into the lungs which is a critical complication especially for seriously ill patients.

The causes for reflux are multiform. Often, during early infancy, they are an expression of an immaturity of the development of the motoric co-ordination of the gastrointestinal tract. In general, with all serious diseases entailing disturbances of the state of consciousness or a drop in the blood pressure, a reflux might occur. This is also the case when the state of consciousness is influenced by medicines, such as, for example, during narcosis. Another large group in which reflux is observed, is patients with a disturbed cerebral function.

Apart from the medical influence on the gastrointestinal motility in particular by means of medicines, which exercises an influence on the autonomic nervous system, two approaches are traditionally pursued with dietetic treatment. The most usual approach is the thickening of the food with galactoglucomannans (taken as a rule from carob beans). This dietetic principle consists in that the thickening of the food practically "mechanically" prevents the stomach contents from flowing back into the oesophagus. The other approach, in particular applied on patients facing the risk of aspiration, consists of making the food extremely fluid so as to allow for a rapid passage through the stomach.

Both approaches, however, are not the best possible. For seriously ill adult patients, it is discussed that fat resorption might possibly be disturbed by the thickening of the food with galactoglucomannans. The disadvantage of extremely liquid food resides in that they are susceptible to offering proteins only in a hydrolyzed form or in very low concentrations. Thus, a sufficient protein supply may not be obtained with such food.

The modifying of proteins and, for example, at least partially to dephosphorylate them so as to decelerate the digestion process, is also already known (WO 97/05785).

It is the task of the present invention to point out a novel approach as to how adult and adolescent patients, as well as babies and small children suffering from a disturbed gastrointestinal motility and reflux-predisposed patients can be nourished in such a way that a sufficient protein supply is ensured and at the same time to allow the food taken in to pass down to the stomach in a rapid way and without running the risk of a reflux.

This task is solved by the teaching of the present claims.

Conventional proteins or protein sources, which are usually used for the production of foods or food products serve as the basic material for the inventive protein component, which may likewise be designated as protein composition or protein mixture. Thereby, in particular natural raw materials of animal or vegetable origin are used. The proteins used may thereby be of any optional type.

At least 20 wt-% and hence 20 to 100 wt-% of the proteins used for the production of this protein component are those comprising at least one phosphate residue, which is covalently bound to the corresponding protein. In an advantageous manner, cow milk proteins are thereby concerned, and in particular the caseins thereof. The remaining proteins and hence 0 to 80 wt-% are those, which "right from the very beginning" and hence by nature do not comprise covalently bound phosphate group/s.

According to the present invention, 50 to 100 wt-% of those proteins comprising at least one covalently bound phosphate residue, are then subjected to a dephosphorylating reaction known per se, during which 20 to 100% of the covalently bound phosphate residues are split up. In other words, the covalently bound phosphate content of those proteins, which were subjected to a dephosphorylating reaction, are reduced by 20 to 100%, preferably by 20 to 85%.

The protein component used according to the present invention is therewith composed of
  a) 20 to 100 wt-% of proteins, which originally comprise at least one phosphate residue, and of which
    i) 50 to 100 wt-% were subjected to a dephosphorylating reaction during which 20 to 100% of said phosphate residues were removed, and
    ii) 0 to 50 wt-% were not subjected to such a dephosphorylating reaction, and
  b) 0 to 80 wt-% of proteins, which are free of a phosphate residue from the very beginning.

The weight ratio between proteins a) and proteins b) is thereby preferably 30:70 to 50:50 and in particular about 40:60.

When a range is mentioned within the scope of the present documents such as for example the above-mentioned ranges of 20 to 100 wt-%, 50 to 100 wt-%, 0 to 50 wt-% and 0 to 20 wt-%, as well as with the described dephosphorylation degrees of 20 to 100% or 20 to 85%, all intermediate single values, in particular all integral single values, and even all smaller ranges comprised thereof, are therewith disclosed. A part of these disclosed single values (in % or wt-%) are for example 1, 2, 3, 4, 5 . . . , 9 . . . , 13 . . . , 17, 18 . . . , 21, 22, 23, 24, 25, 26 . . . , 31, 32, 33 . . . , 38, 39,40, 41 . . . , 48, 49, 50, 51, 52, 53, 54, 55 . . . , 68, 69, 70, 71 . . . , 78 . . . , 83, 84 . . . , 88, 89, 90, 91 . . . , 95, 96, 97, 98 and 99. Comprised ranges are for example 20 to 40, 30 to 50, 40 to 85, 45 to 75, 50 to 85, 40 to 75, 50 to 85, 55 to 90, etc. These aforementioned ranges are given as a mere example.

The protein component used according to the present invention may be administered as such to a patient and hence as the sole component or protein component, for example in the form of tube nutrition. In an advantageous way, however, the protein component according to the present invention will further be mixed with the other usual components of a nutrition, and in particular with an instant food product, and is then given to the patient in a form incorporated in a nutrition. The protein component according to the present invention can thereby either constitute the only protein component of such a food or it can also be mixed with further protein components.

The protein component used according to the present invention can thereby be used in such a form that, apart from dephosphorylation, it is not subjected to any further treatment.

However, the protein component can also be subjected to a further treatment known per se prior or subsequent to dephosphorylation.

The invention is based on the surprising finding that by means of a gradual enzymatic dephosphorylation of the protein source used with a dephosphorylation degree of 20 up to a maximum of 100%, and in particular of 20 to 85% and, if necessary, by mixing these dephosphorylated proteins with non-dephosphorylated proteins comprising phosphate residues and/or with proteins comprising no phosphate residues or phosphate groups by nature, stomach emptying can be selectively controlled. A correspondingly faster emptying of the stomach will, in turn, considerably reduce reflux. By means of the selective control of the degree of the dephosphorylation, one has moreover the possibility to specifically respond to various disturbances of the gastrointestinal motility.

For the production of baby foods/infant formulae and tube foods, cow milk proteins are usually used as the protein source. These cow milk proteins are comprised of caseins and lactoserum proteins. Caseins are distinguished from lactoserum proteins particularly in that they coagulate in an acid environment (pH value of below 4.8), cluster into larger aggregates and deposit in liquids. The proteins remaining in the supernatant liquid are the lactoserum proteins.

Said coagulation also takes place in the human stomach, which exhibits a pH value of between 2 and 4 depending on the human being's age. The type of the coagulation occurring in the stomach quite obviously depends on the structure of the casein molecules, which inter alia is determined by the covalently bound phosphate content. Cow milk caseins are rich in covalently bound phosphate.

For this reason, caseins are used as the protein source, in particular bovine caseins.

The dephosphorylation may ensue chemically or enzymatically. With chemical dephosphorylation, the covalently bound phosphate is cleaved off by the action of heat (preferably between 120 and 140° C.) and/or an increase of the pH value (pH preferably between 10 and 12). The disadvantage of this chemical modification resides in that, due to the high temperatures, peptide bonds are cracked, i.e. that the casein is partially hydrolyzed. By increasing the pH value, a masking occurs, in particular of the lysine ε-amino group (formation of lysino alanine), leading to a reduction of the biological valency of the protein. For the enzymatic dephosphorylation, the alkaline or the acid phosphatase are available. The alkaline phosphatase is preponderantly obtained from biological materials such as small intestine mucosa, liver, kidney, blood and microorganisms. These preparations, however, frequently exhibit the disadvantage of not being free from proteases. This leads to a partial hydrolysis of the casein during dephosphorylation. Significantly more appropriate is, for example, the acid phosphatase obtained from potatoes. These preparations are free from protease and consequently do not entail any alterations of the casein.

A preferred embodiment of the present invention consists in producing proteins by means of a selective dephosphorylation of bovine caseins, which can serve as the basis for the production of foods for reflux-predisposed persons (babies, children, patients with specific symptoms). Since the amino-acid composition of the caseins remains unaltered with a corresponding implementation of the dephosphorylation, its nutritive value does not change either. For this reason, they can be used in equal quantities as conventional caseins.

The correspondingly dephosphorylated proteins, preferably casein, may be used alone or as a structural element for optional protein mixtures. Apart from the partially dephosphorylated proteins, preferably based on caseins, other proteins, e.g. lactoserum proteins, soybean proteins or other proteins of vegetable or animal origin may be used in these protein mixtures as well. The mixtures depend on the requirements of the respective target groups (babies, small children, adults, specific patients).

Two examples for a selective dephosphorylation of bovine casein are given in the following.

EXAMPLE 1

Bovine sodium caseinate (3% solution) is incubated for two hours at 45° C. with acid phosphatase from potatoes (10 U/g casein). The thereby obtained phosphate cleavage/elimination is 58.5%. The dephosphorylated casein is admixed with lactoserum proteins (ratio of casein proteins and lactoserum proteins 40:60) and the usual components for baby milk. The amino-acid composition of the protein mixture is summarized in the following Table.

Amino-acid composition of the protein mixture for a starter baby food with dephosphorylated casein and lactoserum proteins (40:60)

| amino-acid | g/100 g amino acids |
|---|---|
| asp | 8.9 |
| glu | 18.3 |
| ser | 5.2 |
| his | 2.4 |
| Gly | 1.9 |
| thr | 5.7 |
| arg | 2.7 |
| ala | 4.1 |
| tyr | 3.1 |
| val | 6.0 |
| met | 2.5 |
| ile | 5.8 |
| phe | 4.0 |
| leu | 9.7 |
| lys | 8.5 |
| pro | 8.1 |
| cys | 1.5 |
| trp | 1.6 |

EXAMPLE 2

Bovine potassium caseinate (5% solution) is incubated for one hour at 45° C. with acid phosphatase from potatoes (5 U/g casein). The thereby obtained phosphate elimination is 28.2%. This dephosphorylated casein is used without any addition of further proteins for the production of a typical tube nutrition in the case of a slightly reduced gastrointestinal motility. The amino-acid composition corresponds to that of commercial potassium caseinate.

What is claimed is:

1. A method of treating a patient suffering from disturbed gastrointestinal motility, a reflux-predisposed patient or a patient suffering from both, which comprises administering to said patient an effective amount of a nutritious composition containing conventional food proteins wherein at least 20 weight % of said proteins have at least one phosphate residue being covalently bound to the protein, with 50–100 weight % of the proteins comprising at least one covalently bound phosphate residue having been subjected to a dephosphorylation reaction in which 20–100% of the covalently bound phosphate residues have been eliminated.

2. The method of claim 1, characterized in that 20 to 85% of the covalently bound phosphate residues have been eliminated by means of dephosphorylation.

3. The method of claim 1, characterized in that enzymes of the phosphates class have been used for dephosphorylation.

4. The method of claim 3, characterized in that acidic phosphatases have been used for the enzymatic dephosphorylation.

5. The method of claim 1, characterized in that the proteins subjected to dephosphorylation are caseins.

6. The method of claim 1, characterized in that the weight ratio a):b) ranges from 30:70 to 50:50, with
- a) being the sum of those proteins which
  - i) carry covalently bound phosphate resides and have not been subjected to dephosphorylation, and
  - ii) have been subjected to dephosphorylation,
- b) being the sum of those proteins that do not initially comprise any phosphate residues.

7. The method of claim 6, characterized in that the weight ratio a):b) is about 40:60.

8. The method according to claim 1, characterized in that the protein component is incorporated in a food product or represents the entire protein component of said food product.

9. The method of claim 5, characterized in that the proteins subjected to dephosphorylation are caseins, which are bovine caseins.

10. The method according to claim 1, wherein the patient is an adult human suffering from disturbed gastrointestinal motility.

11. The method according to claim 7, wherein the patient is an adult human suffering from disturbed gastrointestinal motility.

12. The method according to claim 1, wherein the patient is an adult human who is reflux-predisposed.

13. The method according to claim 1, wherein the patient is an adult human who is reflux-predisposed.

14. The method according to claim 7, wherein the patient is an adult human who is reflux-predisposed.

15. The method according to claim 1, wherein the patient is an adult human and the administering is by oral administration.

* * * * *